United States Patent [19]

Anshus

[11] 4,115,399

[45] Sep. 19, 1978

[54] PREPARATION OF CATALYST FOR THE POLYMERIZATION OF 2-PYRROLIDONE

[75] Inventor: Byron E. Anshus, Orinda, Calif.

[73] Assignee: Chevron Research Company, San Francisco, Calif.

[21] Appl. No.: 668,888

[22] Filed: Mar. 22, 1976

[51] Int. Cl.$^2$ .......................................... C07D 207/26
[52] U.S. Cl. ...................... 260/326.5 FN; 252/431 N
[58] Field of Search .............................. 260/326.5 FN

[56] References Cited

U.S. PATENT DOCUMENTS

| | | |
|---|---|---|
| 3,563,980 | 2/1971 | van Mourik et al. ....... 260/326.5 FN |
| 3,681,293 | 8/1972 | Jarovitzky ........................... 260/78 P |
| 3,778,402 | 12/1973 | Kimura et al. ..................... 260/78 P |

*Primary Examiner*—Donald G. Daus
*Assistant Examiner*—Mark L. Berch
*Attorney, Agent, or Firm*—Dix A. Newell; Lawrence S. Squires

[57] ABSTRACT

A catalyst solution for the anionic polymerization of 2-pyrrolidone is produced by contacting an alkali metal hydroxide and excess 2-pyrrolidone. The catalyst solution is dehydrated under stripping conditions.

3 Claims, No Drawings

PREPARATION OF CATALYST FOR THE POLYMERIZATION OF 2-PYRROLIDONE

BACKGROUND OF THE INVENTION

1. Field of the Invention

In the anionic (alkaline-catalyzed) polymerization of 2-pyrrolidone, alkali metal hydroxides, particularly sodium and potassium hydroxide, have commonly been used as sources of alkaline catalyst. The reaction of the hydroxide with 2-pyrrolidone produces the alkali metal pyrrolidonate catalyst, and, as a by-product, water. The reaction is believed to be represented by, e.g., for KOH, the following equation:

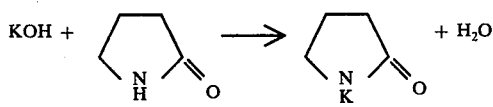

The reaction is typically carried out by contacting the hydroxide in solid form, or in aqueous solution, with excess liquid 2-pyrrolidone to form a solution of alkali metal pyrrolidonate and water in 2-pyrrolidone. The solution is then dehydrated to produce a substantially anhydrous solution of alkali metal pyrrolidonate catalyst in 2-pyrrolidone. Elevated temperatures are used to effect dissolution of the hydroxide in 2-pyrrolidone and subsequent dehydration of the solution. The catalytic properties of the solution are normally found to be sensitive to temperature and water content.

Evaporative and distillative dehydration conditions lend themselves to the loss of appreciable amounts of 2-pyrrolidone with the water removed from the catalyst solution, as well as causing hydrolysis of 2-pyrrolidone remaining in the catalyst solution. Both the loss of 2-pyrrolidone and its hydrolysis are the principal causes of inefficiency in catalyst preparation by this method.

Hydrolysis of the sensitive 2-pyrrolidone ring, which occurs even under mild conditions of heating aqueous 2-pyrrolidone, produces the polymerization inhibitor 4-aminobutyric acid (also see U.S. Pat. No. 3,778,402). On the other hand, dehydration of 2-pyrrolidone to dimer, which is said to occur even under mild conditions of prolonged heating of anhydrous 2-pyrrolidone, produces polymerization initiators which cause "runaway polymerization" with the production of low-molecular-weight polypyrrolidone (see U.S. Pat. No. 3,184,476).

2. Prior Art

It has been the usual practice to dissolve solid hydroxide, typically in the form of KOH pellets (85% KOH), in excess 2-pyrrolidone and to remove water under conditions of reduced pressure (see U.S. Pat. Nos. 2,739,959 and 3,721,652). U.S. Pat. No. 2,739,959, for example, discloses the production of catalyst for the anionic polymerization of 2-pyrrolidone by contacting 1 part of KOH pellets with excess (200 parts) of 2-pyrrolidone and removing the water of reaction by distilling off 20 parts of the mixture at a temperature between 90° and 120° C. and a pressure between 0.5 and 10 mm. Potassium hydroxide may also be contacted with excess 2-pyrrolidone in the form of an aqueous solution (see U.S. Pat. No. 3,778,402).

U.S. Pat. No. 3,563,980 discloses a process for preparing a mixture of lactam and an alkali metal compound of this lactam by reacting the hydroxide with the lactam and evaporating the water of reaction by heating in vacuo. It is noted therein that the drawback to the use of a hydroxide is the formation of water, because it must be removed quickly by heating in vacuo to avoid the occurrence of side reactions whose products weaken the activity of the catalyst. It is also noted therein that the rapid removal of water results in the loss of considerable amounts of lactam as well as water.

In the process of U.S. Pat. No. 3,681,293, the catalyst solution is passed to a wiped-film evaporator for dehydration. The evaporator is operated at reduced pressure at as low a temperature as possible. In order to assure that the solution is dehydrated, a mixture of water and 2-pyrrolidone is removed. The problem of hydrolysis of 2-pyrrolidone by KOH and water at elevated temperatures is dealt with by using two evaporators in series, with only the last evaporator operated at temperatures over 80° C.

SUMMARY OF THE INVENTION

A process for the production of a mixture of 2-pyrrolidone and a 2-pyrrolidonate salt serving as a catalyst for the polymerization of 2-pyrrolidone in which a hydroxide, preferably an alkali metal hydroxide such as potassium hydroxide, is contacted with excess 2-pyrrolidone to form a solution of 2-pyrrolidonate and water in 21 -pyrrolidone, and the solution is dehydrated under stripping conditions at elevated temperatures.

BRIEF DESCRIPTION OF PREFERRED EMBODIMENTS

In the process of the present invention, alkali metal pyrrolidonate in 2-pyrrolidone solution is dehydrated at elevated temperatures under stripping conditions. Stripping conditions are used to encourage liquid-vapor contact between the water-containing solution and the stripping gas. The stripping gas is preferably a countercurrently flowing inert gas, or vaporized-liquid, stream. Stripping conditions may be applied to either an evaporative dehydration process or a distillative dehydration process.

In an dehydration process, an alkali metal hydroxide (e.g., KOH) in the form of a solid such as 85% KOH pellets (15% water and/or inert material), or in the form of an alcoholic or aqueous solution of KOH, is contacted with excess 2-pyrrolidone in a reaction zone, such as an agitated reaction vessel, at a temperature of 25°–100° C., preferably below about 80° C. Complete dissolution, or mixing, of the hydroxide in the excess 2-pyrrolidone is effected to form a solution, which, exclusive of added water, normally contains from 0.5 to 30 mol percent KOH based on 2-pyrrolidone, preferably 5 to 20 mol percent KOH and most preferably about 10 mol percent KOH.

The solution of potassium pyrrolidonate and water in 2-pyrrolidone is fed to the dehydration zone, which in the case of evaporative dehydration comprises at least one evaporator, preferably a thin-film evaporator, and most preferably an agitated or wiped-film evaporator (Kirk-Othmer, Encyclopedia of Chemical Technology, 2d Ed., Vol. 8, p. 559). The evaporator is operated at reduced pressures of about 1–100 mm Hg, preferably at about 1–30 mm, and at an elevated temperatures of about 75°–150° C., preferably 75°–105° C. The temperature is that of the catalyst solution removed from the bottom of the evaporator. Stripping is provided by a countercurrently flowing dry inert gas stream, such as nitrogen or helium, which is bled into the evaporator near the catalyst solution outlet at the bottom of the evaporator. The dry inert gas stream flows through the evaporator and is in contact with the catalyst solution. The stripping gas stream preferably flows countercurrently to the liquid flow of 2-pyrrolidonate solution in the evaporator. The inert gases exit with the overhead, comprising water and a small amount of 2-pyrrolidone, to vacuum. The volumetric throughput of stripping gas is normally chosen to achieve the desired degree of dehydration in a reasonably short dehydration time.

The desired degree of dehydration is represented by a catalyst solution having less than about 0.1–0.2 weight percent water. In order to achieve the desired degree of dehydration without the use of a stripping gas, or additional stages of evaporation (U.S. Pat. No. 3,681,293, Col. 8, line 14), it is necessary to lose appreciable quantities of 2-pyrrolidone taken overhead with the water. As much as 30% or more of the 2-pyrrolidone may be lost in a dehydration without the use of a stripping gas. But in evaporative dehydration under stripping conditions, there is no appreciable loss of 2-pyrrolidone, and hydrolysis of 2-pyrrolidone under the influence of water, hydroxide and elevated temperatures, either does not occur, or does not occur to an extent which presents a problem in polymerization.

In a distillative dehydration process, the catalyst solution is prepared as described and fed to a dehydration zone comprising at least one distillation column having a stripping section as well as a rectifying section. That is, the feed is charged at an intermediate position in the column so that stripping is provided in the lower section of the column beneath the feed inlet. The column may be a sieve tray, bubble tray or packed column. Preferably the column is a tray column having at least 4–10 actual trays. At least two trays are below and at least two trays are above the feed inlet. Additional stripping may be provided by countercurrently flowing inert gas streams, but this is not generally necessary. The column is normally operated at a reboiler temperature of about 75°–150° C. and at pressures of about 1–100 mm, preferably at 1–30 mm and most preferably at temperatures and pressures of about 75°–105° C. and 1–5 mm. The reboiler temperature is equivalent to the temperature of the catalyst solution removed from the bottom of the thin-film evaporator, and is the temperature of the solution in the reboiler of the distillation column.

Use of stripping conditions in a distillative dehydration of the catalyst solution is found to allow the use of higher temperatures, i.e., generally over 90° C., without the production of undesirable by-products, as well as providing the desired degree of dehydration without the loss of appreciable 2-pyrrolidone. The avoidance of stripping conditions by feeding the catalyst solution at the bottom of the distillation column is believed to result in the production of undesirable by-products over the time period necessary to effect the desired degree of dehydration of the solution.

While the catalyst solution being dehydrated is normally derived from contacting an alkali metal hydroxide with 2-pyrrolidone, other sources of catalyst may be used, such as by substituting in whole or in part a quaternary ammonium hydroxide such as tetramethyl ammonium hydroxide or an alkaline earth hydroxide such as calcium or barium hydroxide, for the alkali metal hydroxide. However, sodium and potassium hydroxide are preferred as sources of alkaline catalyst, and potassium hydroxide is most preferred.

The dehydration of catalyst solutions according to the process of the present invention may be a step in a discontinuous, i.e., batchwise polymerization process, or it may be carried out continuously (for example, see U.S. Pat. Nos. 3,681,293, 3,721,652 and 3,804,813).

EXEMPLIFICATION

Example 1

A catalyst mixture containing 1000 g of 2-pyrrolidone, 52 g of KOH and 65 g of water was continuously fed to a wiped film evaporator operated at 5 mm pressure. Heat input to the evaporator was adjusted until the bottoms product consisting of potassium pyrrolidonate and 2-pyrrolidone had a water content of less than 0.2 weight percent. The temperature was within the specified range of less than 150° C. Under these conditions about 28% of the 2-pyrrolidone fed to the evaporator in the catalyst mixture was being continuously evaporated and lost overhead together with the water. Using the catalyst so produced (at about 10 mol percent), together with $CO_2$ (at about 3 mol percent), gave a satisfactory polymerization rate of about 1% conversion per hour to a polypyrrolidone of high molecular weight.

Example 2

The catalyst mixture of Example 1 was continuously fed to the wiped film evaporator of Example 1 while simultaneously a small stream of dry nitrogen was continuously bled into the evaporator near the bottoms outlet. The heat input was adjusted as in Example 1 to provide a bottoms product having a water content of less than 0.2 weight percent. However, under these conditions, substantially the same as those of Example 1 except for the use of a stripping gas stream, only 1% of the 2-pyrrolidone fed to the evaporator in the catalyst mixture was lost overhead. The 28-fold improvement over Example 1 is entirely attributed to the use of stripping conditions. Using this catalyst, the rate of conversion and the molecular weight of the polypyrrolidone was substantially as in Example 1.

Example 3

A catalyst mixture containing 800 g of 2-pyrrolidone, 52 g of KOH and 65 g of water was continuously fed at 7.7 ml/min. to the center plate of a 10-plate, 2-inch diameter glass distillation column with a one liter stainless steel reboiler. The feed was made to the center of the distillation column in order to utilize the stripping conditions present in the lower one-half of the column. The utilization of stripping conditions in the column was found to have the net effect of decreasing the time required to reduce the water content in the catalyst. The column operated at 5–20 mm absolute pressure and the reboiler temperature was 139° C. The water concentration in the bottoms product was found to be less than 100 parts per million (ppm) and less than 0.1 weight percent of the 2-pyrrolidone fed to the column in the catalyst mixture was lost overhead with the water. Using this catalyst, the rate of conversion to polypyrrolidone was 1.3% per hour and the polymer was of high molecular weight.

What is claimed is:
1. The process for the production of a mixture of 2-pyrrolidone and a 2-pyrrolidonate salt serving as a catalyst for the anionic polymerization of 2-pyrrolidone, comprising the steps of:

contacting in a reaction zone a hydroxide and excess 2-pyrrolidone to produce a solution of 2-pyrrolidonate and water in 2-pyrrolidone, conducting said solution through an evaporative dehydration zone comprising a thin-film evaporator;

dehydrating said solution under stripping conditions at a temperature of about 75°–150° C. and pressure of about 1–30 mm by flowing a dry inert gas stream countercurrently to the flow of said solution through said thin-film evaporator; and collecting a bottoms product from said thin-film evaporator containing less than about 0.2 weight percent water, without appreciable loss of 2-pyrrolidone.

2. The process according to claim 1 wherein said hydroxide is an alkali metal hydroxide or a quaternary ammonium hydroxide.

3. The process according to claim 2 wherein said alkali metal hydroxide is potassium hydroxide.

* * * * *